United States Patent
Schellekens et al.

(10) Patent No.: US 8,689,606 B2
(45) Date of Patent: Apr. 8, 2014

(54) GAS SENSING USING ULTRASOUND

(75) Inventors: Martijn Schellekens, Eindhoven (NL); Josephus Arnoldus Henricus Maria Kahlman, Tilburg (NL); Martinus Gernardus Van Der Mark, Best (NL); Peter Dirksen, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 162 days.

(21) Appl. No.: 13/203,987

(22) PCT Filed: Mar. 10, 2010

(86) PCT No.: PCT/IB2010/051043
§ 371 (c)(1),
(2), (4) Date: Aug. 31, 2011

(87) PCT Pub. No.: WO2010/109363
PCT Pub. Date: Sep. 30, 2010

(65) Prior Publication Data
US 2011/0314897 A1 Dec. 29, 2011

Related U.S. Application Data

(60) Provisional application No. 61/162,361, filed on Mar. 23, 2009.

(51) Int. Cl.
*G01N 29/02* (2006.01)
(52) U.S. Cl.
USPC .......................................................... 73/24.01
(58) Field of Classification Search
USPC ............................................ 73/24.01, 24.06
See application file for complete search history.

(56) References Cited

U.S. PATENT DOCUMENTS

| | | | |
|---|---|---|---|
| 3,981,176 A * | 9/1976 | Jacobs | 73/24.01 |
| 5,982,709 A | 11/1999 | Ladabaum et al. | |
| 8,068,623 B2 * | 11/2011 | Lesso | 381/123 |
| 2002/0026937 A1 | 3/2002 | Mault | |
| 2003/0149363 A1 * | 8/2003 | Dreschel et al. | 600/437 |
| 2004/0050142 A1 * | 3/2004 | Hok | 73/23.21 |
| 2005/0075572 A1 | 4/2005 | Mills et al. | |
| 2005/0146247 A1 * | 7/2005 | Fisher et al. | 310/334 |
| 2007/0164631 A1 | 7/2007 | Adachi et al. | |
| 2008/0271543 A1 * | 11/2008 | Hecht et al. | 73/861.27 |

OTHER PUBLICATIONS

Stagger tuned cMUT array for wideband airborne application, Selim Olcum et al., 2006 IEEE Ultrasonics Symposium, p. 2377.
J.A.M. van de Nieuwendijk and J.E.M. Vael, "Bass-Reflex Port Measurements," Nat.Lab. Technical Note TN 065/97 and in "Alles wat ademt—R.de Nijs," EMI 1984.
Park et al., "Capacitive Micromachines Ultrasonic Transducers for chemical Detection in Nitrogen", 2007 American Institute of Physics, Applied Physics Letters 91.

* cited by examiner

*Primary Examiner* — Hezron E Williams
*Assistant Examiner* — David Z Huang

(57) ABSTRACT

A sensor chip (1030) for gas has cells (200) for emitting and receiving ultrasound and is configured for a sufficiently large frequency range and for measuring concentration of at least one of the gas components based on at least two responses within the range. The frequency range can be achieved by varying the size of cell membranes (230), varying bias voltages, and/or varying air pressure for an array (205) of cMUTs or MEMS microphones. The sensor chip can be applied in, for example, capnography. A measurement air chamber (515) is implemented in the respiratory pathway (400), and it and/or the pathway may be designed to reduce turbulence in the exhaled breath (120) subject to ultrasound interrogation. The chip (1030) can be implemented as self-contained in the monitoring of parameters, obviating the need for off-chip sensors.

20 Claims, 14 Drawing Sheets

GAS SENSING USING ULTRASOUND

FIELD OF THE INVENTION

The present invention relates to analyzing multi-constituent gas using ultrasound, and, more particularly, to using a single chip to perform the analysis.

BACKGROUND OF THE INVENTION

The analysis of exhaled breath is an important monitoring tool in modern hospital settings. Through the analysis of fluid mechanical properties such as flow and volume, information about pulmonary functions can be extracted. As the lungs are the location where the gasses are exchanged between blood and air, the difference of major air constituents such as $O_2$, $CO_2$ and $H_2O$ between inhaled and exhaled breath are indicative of the arterial blood gases. Also the blood diffusion of anesthetic agents can be followed through breath analysis. Finally, trace markers such as NO can relate on pathologies within the lungs or airway.

The measurement of $CO_2$ in exhaled breath is known as capnography. Carbon dioxide is produced in the body through aerobic metabolism. It is then transported by blood flow to the heart and then the lungs, before being exhaled. If the patient is on a respirator, the $CO_2$ continues along a respiratory pathway to the respirator. En route or at the respirator the level of $CO_2$ is measured. The $CO_2$ is removed and $O_2$ is supplied in the cycle back to the patient's respiratory system. The oxygen is absorbed by the lungs into the blood. The blood is pumped by the heart, thereby transporting the oxygen throughout the body. The cycle continues as cells of the body produce $CO_2$ which is then transported by blood flow.

Capnography measurements are particularly important in emergency and surgical procedures and for long-term respiratory assistance.

It is needed to identify correct positioning of an endotracheal tube or laryngeal mask. Failure to detect a faulty positioning can very serious or fatal.

The ASA (American Society of Anesthesiologists) recommends capnography for every patient receiving general anesthesia, and, more generally, for continual monitoring and the identifying of correct positioning of tubes or masks with respect to the patient in establishing a cyclical respiratory pathway.

The level of $CO_2$ in exhaled breath is an indicator that helps in diagnosing hypoxia, i.e., insufficient oxygen in the blood, so that countermeasures can expeditiously be taken before the medical subject suffers irreversible brain damage. Hypoxia can occur when, for example, a conscious but sedated patient becomes over-sedated and slips into unconsciousness that results in respiratory obstruction. In such a situation, respiratory obstruction can be detected early via capnography, whereas hypoxia (which is detectable through pulse oximetry) occurs considerably later, when the time left to remedy the situation is short.

Capnography, can, for instance, also detect circulatory failure, e.g., cardiac arrest. If blood is not delivered to the lungs, the level of $CO_2$ in exhaled breath drops. This can be detected early through capnography, so that resuscitation can be commenced.

$CO_2$ is also the main contributor to the pH level in the blood. The body regulates the breathing rate according to the pH level.

Other major constituents of air are oxygen, water vapor and nitrogen. Oxygen levels, like carbon dioxide levels, have clinical significance, but can be adequately monitored on the input (i.e., inspiration) side. Under some circumstances, water vapor levels also assume clinical significance, as with the asthmatic patient.

Other gases encountered in exhaled breath include ethanol, ingested through a liquid substance, and anesthetic vapors, the anesthetic having been administered to prepare for surgery and being supplied continuously at lower levels during the procedure.

Capnography can be done in either of two distinct measurement configurations, namely the mainstream and the sidestream configuration. In the mainstream configuration, the gas sensor device is placed on the tube that goes into the airway of the patient. It measures the entire flow and has a fast response. It does require, though, that an endotracheal tube is been placed in the patient. The sidestream configuration on the other hand uses a small tube that extracts at a continuous pace some air from the airway from the patient. That air then goes via a sample line to an offside module where the sensor is placed. Because of the gas transport, the sidestream configuration has a slower response than the mainstream configuration, yet by placing the tube right at the exit of the nose and mouth, sidestream provides a less invasive technique. However, since the introduction of very low volume sample lines, the lower time resolution associated with sidestream is no longer valid.

The first analysis of gases with ultrasound goes back to the 1920's, when both quartz ultrasound transducers and stable frequencies became largely available.

The detection technology generally used for $CO_2$ detection (capnography) is Non-Dispersive Infra Red absorption (NDIR) at 4.3 nanometers (nm) (i.e., the wavelength absorbed by $CO_2$). It is perceived as being the only technology that meets the (60-100 ms) time-resolution and specificity demands Chemical detection is also possible and generally cheaper, but it brings classically longer time constants along which prevent time-resolution demands from being met.

A difficulty with ultrasound lies in the ability of a solid to transfer its movement to a gaseous medium. This transfer is generally highly inefficient in terms of energy, because of an impedance mismatch between the ultrasound transducer and the gaseous medium.

Piezoelectric transducers are commonly used to transmit and receive ultrasound, but face this inefficiency if the medium is gaseous.

The capacitive micromachined ultrasonic transducer (cMUT) provides a better impedance match to fluid media.

Researchers at Bilkent University have studied using cMUTs in fluid media for air-borne applications. "*Stagger tuned cMUT array for wideband airborne application,*" Selim Olcum et al., 2006 *IEEE Ultrasonics Symposium*, pg. 2377. They found that since the center frequency of a cMUT element depends on its radial size, a 60% bandwidth in air is possible when different sized cMUTs are connected in parallel. Using more transducer elements with different cell radii further increases the bandwidth, but the study does not indicate by how much.

SUMMARY OF THE INVENTION

In the case of a molecular gas, the translational energy associated to an ultrasound wave can also be transferred to the rotational and vibrational energy levels of the molecules. As there is a time constant involved, this results through a relaxation process in a frequency dependent sound absorption and speed. As the rotational and vibrational configuration depends on the molecule, and the transfer mechanisms depend on the species involved in the collisions, the measurement on the spectral non-classical sound properties makes it possible to distinguish between different gases. In particular, $CO_2$ has an interesting signature in terms of sound speed and absorption, at standard pressure and temperature.

Air ultrasound transducers normally only operate at fixed frequencies. If one therefore wants to study the spectral performances of a gas at different frequencies, one has to implement either various ultrasound transducers, or one has to modulate isothermally the pressure inside the gas (from a theoretical point of view, isothermal pressure and frequency dependencies are identical). The multi-transducer solution is hard to implement as it results in a costly and bulky system when using standard transducers. The isopressure changing method is generally feasible only in laboratory settings.

The use of a multi-frequency cMUT device for gas analysis makes it possible to perform a spectral study with a single, inexpensive and small device.

Although, as observed by the present inventors, it has been proposed to analyze gas concentrations using ultrasound, using a single frequency entails a huge problem: at one single frequency one can only measure one Time-Of-Flight (TOF) and one absorption coefficient. This fixes at most 2 degrees of freedom in the gas. Air comprises 4 main components: $N_2$, $O_2$, $H_2O$ and $CO_2$, which in combination with pressure, temperature and flow brings the number of parameters to 7.

State-of-the-art gas single-frequency analyzers comprise extra sensors—distributed sensors—to compensate for flow, humidity and temperature, which make them cost expensive, complex, failure sensitive and maintenance intensive.

Furthermore, whereas an ultrasound measurement is necessarily a volume measurement, temperature and humidity sensors often imply a surface measurement. This makes them unsuitable for the application of capnography.

As the present inventors have observed, small sized on-chip ultra-sound transducers cannot be used for capnography measurements because of the required large dimensions of the ultrasound chamber to avoid turbulences and consequentially the long propagation length.

The main two reasons are that small sized transducers are (1) not able to generate enough power to overcome the damping in large pathways and are (2) less able to generate a parallel sound wave so that the reflections are difficult to concentrate on a sensor.

In spite of the benefits of using US (ultrasound) devices for capnography, e.g., a more economical solution than optical sensing, a new problem arises: namely that turbulent gas flow strongly affects the propagation of the sound waves. In state-of-the-art optical or electro-chemical based capnography airway system the flow in the ¾ inch (1.905 cm) diameter pipes is turbulent, but this is no issue for the measurement itself.

When adapting this airway system for an ultrasound based capnography sensor the signal becomes unstable, and extensive averaging is required. This in turn will slow down response time of the device, where from a diagnostic point of view it is required to have a relatively fast response.

The turbulence will disturb the path as well as effective speed of sound through the gas under examination. Hence, noise will be introduced to the measurement of sound speed and sound absorption along the predefined path, in particular if the measurement time is short and sufficient averaging cannot take place.

Normally, in a long uniform tube or channel, it is anticipated that turbulence can occur when the Reynolds number is larger than 2400. The Reynolds number is a measure in fluid mechanics of the ratio of inertial forces to viscous forces.

The Reynolds number Re is defined herein as follows:

$$Re = \frac{uD}{\eta}, \text{ where } \eta = \frac{\mu}{\rho}$$

u=typical speed of the flow [m/s]
D=typical diameter of the tube [m]
$\mu_0$=viscosity of air=$1.846 \cdot 10^{-5}$ [kg/ms].
$\rho_0$=density of air=1.2 [kg/m$^3$].
$\eta$=kinematic viscosity of air=$1.511 \times 10^{-5}$ [m$^2$/s].

All parameters are temperature and humidity dependent. In order to be in the laminar regime, hence without turbulences, the Reynolds number has to be below 2400.

(In the case of rectangular ducts, the Reynolds number is defined in the manner known to those of ordinary skill in the art.)

Furthermore at interfaces, constrictions, expansions, bends or deformations may introduce impedance changes and consequentially turbulence. Furthermore, fast flow variations (due to breathing) pronounce the signal degradation heavily because of the appearance of uncontrolled turbulences.

To put the problem in perspective: in a standard Respironics™ NDIR based mainstream capnography system, a peak flow of $f_{max}$=3 ltr/s in the D=1 cm measurement volume generates an air speed $$u = \frac{4f}{\pi D^2} = 38 \text{ m/s,}$$

which compares to a category-1 hurricane. As a result, the Reynolds number $$Re = \frac{uD}{\eta} = 25000$$

and the flow are highly turbulent. The medical relevance of said category-1 hurricane peak-flow is obvious: capnography sensors aim for measuring the flow waveform, including the peaks.

The minimal tubing diameter $D_{min}$ to maintain laminar flow can be found by reshuffling the Reynolds number formula:

$$D_{min} = \frac{4f_{max}}{\eta \pi Re} = 10.5 \text{ cm}$$

at a peak flow f=3 ltr/s.

As a result at least the detection chamber must pretty large and power hungry, which blocks the use of small sized on-chip ultra-sound devices. Furthermore it makes the application of small sized sensor devices impossible.

Moreover, although the above-mentioned Bilkent University study proposes to cMUTs for airborne applications warranting a bandwidth of up to 60% or beyond, the present inventors have observed that the 60%-bandwidth frequency range is far too small for capnography. The present inventors have further observed that it is very difficult to build an ultrasound transducer with sufficient bandwidth to cover a frequency range suitable for capnography, e.g., from 0.2 to 5 MHz which is sufficient or preferably 0.05 to 10 MHz.

In an aspect of the present invention, a single-chip multi-gas analyzer system avoids the above-described drawbacks.

The present invention is directed to addressing the limitations of the prior art in analyzing a multi-component gas as, for example, in capnography.

To better address one or more of these concerns, and in accordance with an embodiment of the present invention, a sensor chip for gas comprising a plurality of components is configured with cells for emitting and receiving ultrasound and is configured for a sufficiently large frequency range and for measuring concentration of at least one of the plural gas components based on at least two responses within the range.

In one variation, the cells have membranes for said emitting and receiving, each membrane having a size, the membrane sizes differing so as to enable the measuring of the concentration.

In an alternative or supplemental variation, the spring constant of the membrane, which depends on factors such as the membrane tension, the electric field and the air pressure, can be varied among the transducers in order to alter their frequencies. The spring constant k, according to Hooke's law, obeys the formula $F=-kx$, as known by those of ordinary skill in the art.

In a further alternative or supplemental variation, the cells have bias voltages that differ so as to realize varying, among the cells, of the respective frequencies to enable the measuring of the concentration.

In a particular aspect, the sensor chip is configured for, for the gas whose concentration is to be measured, sequentially tuning a cell of over a sufficiently broad range, by varying bias voltage for the cell, to thereby retrieve different ones of the at least two responses.

In implementations of the present invention, a measurement air chamber contains the sensor chip which is configured to adjust to gas pressure in the chamber, and the chamber is configured dimensionally to selectively vary cell-by-cell the gas pressure relative to the cell to thereby alter frequencies of said cells, to achieve the measuring of the concentration of at least one gas component.

The frequency range, in accordance to a version of the invention, extends from 50 kHz to 10 MHz.

In one embodiment, one or more of the cells are configured as a capacitive devices, which may be, for example, cMUTs (capacitive micro machined ultrasound transducers) or MEMS (micro electro mechanical systems) microphones.

In a further aspect, the sensor chip is configured for the measuring of the concentration of all of the gas components.

The invention may be realized as a capnography sensor for measuring a level of carbon dioxide in exhaled breath.

As a particular variation of this, the air flowing is exhaled breath, the sensor chip being further configured for determining ultrasound time-of-flight and such that the measuring of the concentration of the at least one component is performed without the need for an off-chip sensor.

In a further aspect, a sensor chip is designed for emitting ultrasound into air flowing across the membranes, the cells being arranged in a direction of the flow.

In another aspect, a sensor chip for a respiratory pathway has ultrasound transducers configured for interrogating so as to receive at least two responses between 50 kHz and 10 MHz, and is configured for combining the responses to measure the concentration of at least one air component in the respiratory pathway.

In an embodiment of the above, a first of the transducers emits a pulse that is thereafter detected by a second of the transducers, the second transducer likewise emitting a pulse that is thereafter detected by the first transducer, air flow being measurable based on comparison of the detected pulses.

Alternatively, transducers are arranged in a direction of air flow across the sensor chip to receive return data of a diverging ultrasound wave, the sensor chip being configured to compare results of the transducers with respect to time-of-flight and/or amplitude, to measure air flow.

As a further alternative, at least one ultrasound transducer of said plurality is a capacitive device having a pair of plates separated by a gap, the sensor chip being configured for measuring capacitances of the plates to thereby determine air pressure, and therefore air flow.

In one other aspect of the invention, a measurement air chamber is disposed, with respect to air flow, in communication with a respiratory pathway. The air chamber has a sensor chip that includes ultrasound transducers to measure responses between 50 kHz and 10 MHz. The air chamber also has an acoustic impedance profile such that the Reynolds number at any position in the chamber is smaller than 2400 for respiratory flows between −3 and +3 liters per second.

In a corresponding embodiment, the air chamber is configured to measure full mainstream flow, and dimensioned with a minimal diameter of 10.5 centimeters.

In a variation of the above, the air chamber is dimensioned with a minimal diameter of 10.5 centimeters, except that the longitudinal ends of said air chamber taper down to 1.9 centimeters in diameter.

As an alternative, the air chamber is configured with an underpass to split the air flow and to reflect ultrasound emitted from the sensor chip, the sensor chip being disposed below the underpass.

As a variation on this, the underpass can be configured as an on-chip roof.

In a particular version of the above corresponding embodiment, the air chamber diverts a portion of the air flow from the respiratory pathway for circulation back into the respiratory pathway. Furthermore, the air chamber is configured for short cutting some of the diverted portion into a pathway in which the sensor chip is located.

In yet another aspect, an air-constituent measurement chip includes an array of transducers having flexible membranes for emitting and receiving ultrasound, each membrane having a size. The chip is configured for measuring air flow using the transducers in an air flow direction. The chip is further designed for measuring temperature by transducer-plate-based capacitive measurement and/or by on-chip thermopiles or resistive elements. The chip is further configured with bias voltages of the transducers and/or the membrane sizes differing so as to achieve sufficient ultrasound frequency range and for, without need for off-chip sensors, measuring concentrations of nitrogen, oxygen, water and carbon dioxide in air.

In accordance with these, and other, aspects of the present invention, use of an all silicon ultrasound transducer, on-chip, allows the problems of bandwidth, power consumption, cost and weight to be overcome. Moreover, the cMUT technology is CMOS (complementary metal oxide semiconductor)-compatible, so that it can be integrated with the electronics for signal generation and data reduction. For example, it is easy to integrate a pressure sensor. Also, flexibility is gained in that the low-cost chip may be regarded as disposable.

Details of the novel multi-gas, ultrasound-based sensing are set forth further below, with the aid of the following drawings.

DETAILED DESCRIPTION OF EMBODIMENTS

Figure 1:
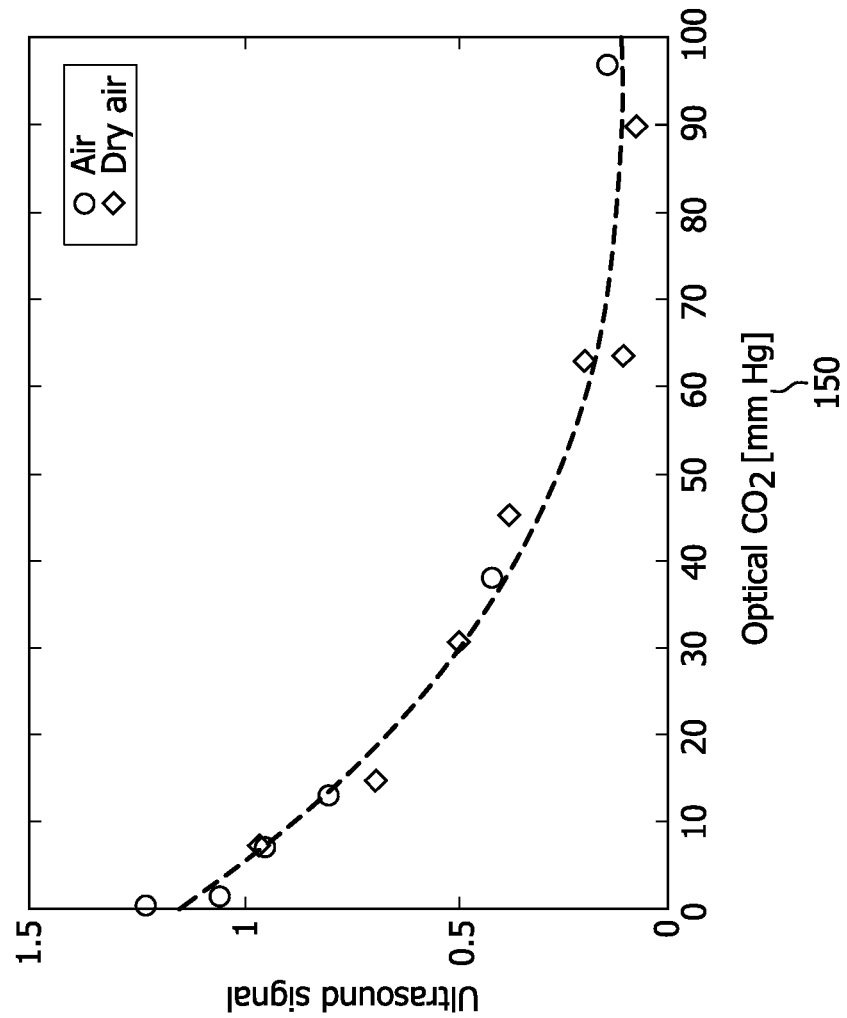
FIG. 1 is a conceptual and graphical diagram making one type of comparison between optical and ultrasound approaches to capnography, in accordance with the present invention.
Figure 1:
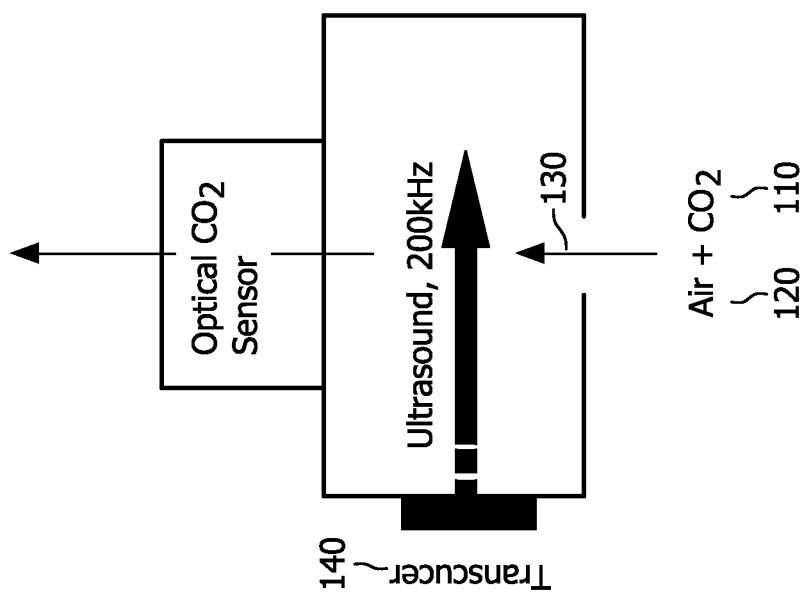

FIG. 1 depicts a conceptual and graphical comparison between optical and ultrasound approaches to capnography, in accordance with the present invention.

Carbon dioxide 110 absorbs IR (infrared) light of a specific wavelength, 4.3 nm. Because the amount of light absorbed is proportional to the concentration of the absorbing molecules, the $CO_2$ concentration is determinable by comparing the measured absorbance with the absorbance of a known standard. The concentration is expressed as a partial pressure (of $CO_2$) in mmHg.

In the ultrasound context, a gas, in particular $CO_2$, has a characteristic absorption spectrum. It is noted that $CO_2$ in air exhibits an absorption maximum between 20 kHz and 2 MHz. By recording the absorption spectrum, i.e., by recording the absorption coefficient of ultrasound versus the ultrasound frequency and by measuring sound speed, the components of a simple gas mixture and their concentrations can be determined Thus it is possible to determine the percentage of $CO_2$ in air. It is noted that determining $CO_2$ percentage entails determining the percentage of other air constituents, particularly the percentage of $H_2O$. The degrees of freedom are determined by the gas mixture itself plus additional parameters like pressure, temperature. So in a mixture of $N_2$ and $CO_2$, for example, at constant humidity, temperature and pressure, the concentration of the two components can be determined by merely two ultrasound responses, in accordance with the present invention, although typically, more than two responses would be combined according to the present invention.

As shown in FIG. 1 exhaled air 120 (which contains $CO_2$) flows 130 past an ultrasound transducer 140 and then an optical $CO_2$ sensor. (This is a conceptual depiction—a novel ultrasound transducer in accordance with the present invention would overcome the need for an optical sensor).

The graph demonstrates that, as the concentration 150 of $CO_2$ in air increases (left to right on the abscissa), the energy of the received RF (radio frequency) signal is lower in magnitude. The decrease is due to greater attenuation, since a larger number of $CO_2$ molecules are absorbing the ultrasound. Since the plotted graph closely tracks a known function, the ultrasound transducer 140 can reliably replace the optical sensor, with the aforementioned advantages, e.g., lower cost.

For analysis of the gas composition, selectivity is realized through the use of several ultrasound frequencies in, for example, the range of 20 kHz through 5 MHz to record an ultrasound spectrum that is characteristic for the gas mixture.

Figure 2:
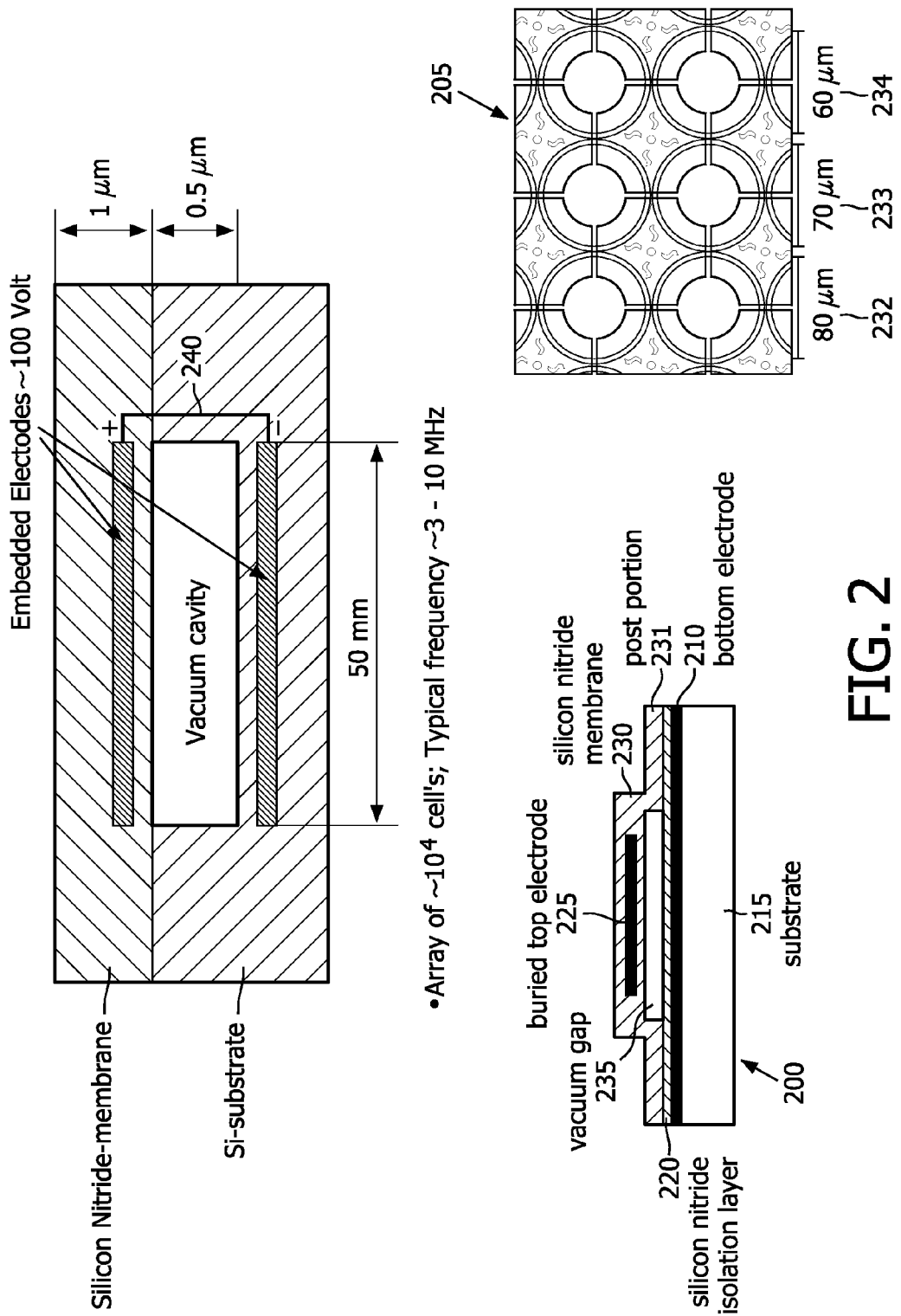
FIG. 2 is, illustratively, a conceptual diagram of a cMUT, a schematic diagram of a cMUT, and a cMUT array, all in accordance with the present invention.

FIG. 2 depicts, by way of illustrative and non-limitative example, a conceptual diagram of a cMUT, a schematic diagram of a cMUT 200, and an array 205 of cMUTs 200, all in accordance with the present invention. The cMUT may be fabricated with a low-temperature, CMOS compatible process, so that is can be integrated with the circuitry for signal generation and data reduction.

The cMUT 200 includes, for example, a bottom electrode 210 embedded between a substrate 215 and a silicon nitride isolation layer 220. A top electrode 225 is embedded within a silicon nitride membrane 230. Supported by an annular post portion 231, a flexible membrane or ultrasound interface surface 230 (having a radius 232, 233, 234) and an isolation layer 220 form a cavity 235 there between. The cavity 235 may be vacuum-sealed or contain a gas. The radii 232-234 are shown as varying in size, which varies the respective center frequencies of the three cMUTs 200. Alternatively, or in addition, a bias voltage 240 may be applied between the electrodes 210, 225 to deflect the membrane 230, and may be varied among cMUTs 200 in the cMUT array 205 to thereby vary the respective center frequencies. In applications other than capnography, where response time is not critical, a single transducer may be sequentially tuned over a sufficiently broad range, by varying bias voltage for the transducer, to thereby provide the frequencies needed to analyze concentration of constituents of a given gas.

The cMUT array 205 may be implemented on an ASIC (application-specific integrated circuit), or SoC (system-on-chip), that includes on-board a DSP (digital signal processor) and, in addition to the transducer array 205, other sensors such as, for example, thermopiles and radar. The resulting sensor chip may be flexible, and could be glued onto flexible foil, the silicon then being ground down.

Figure 3:
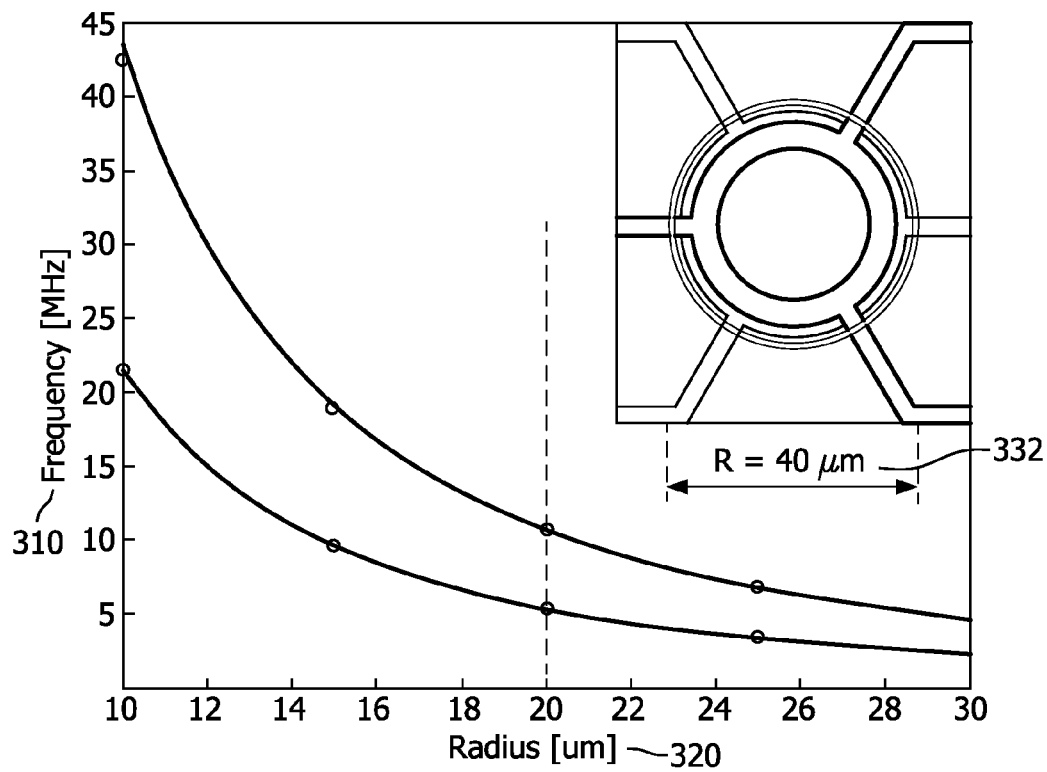
FIG. 3 is one example of a graphical comparison of cMUT ultrasound frequency to membrane radius and air pressure in capnography to capacitance of the plates of a cMUT capnography sensor, in accordance with the present invention.
Figure 3:
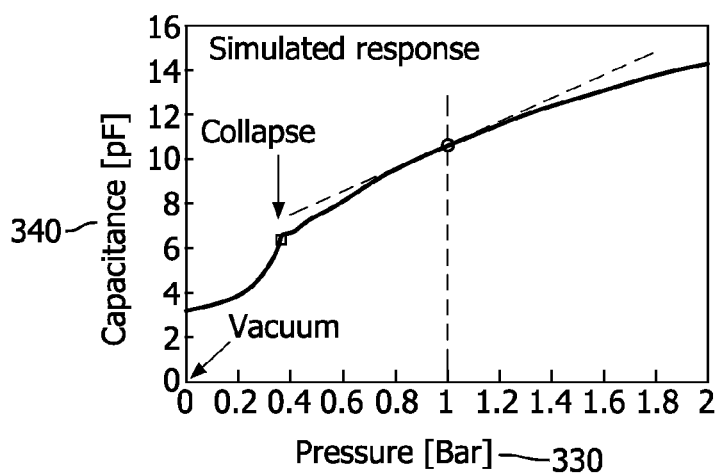

FIG. 3 exemplifies, in accordance with the present invention, a comparison of cMUT 200 ultrasound frequency 310 to membrane size and, in particular, to the radius 320. Further shown in FIG. 3 is an exemplary comparison between air pressure 330 in capnography and capacitance 340 of the plates 220, 230 of a cMUT 200 capnography sensor, in accordance with the present invention.

In the simplest case (low AC driving voltage, low DC bias), the frequency lowest mode of vibration is:

$$f = \frac{10.21}{2\pi R^2}\sqrt{\frac{D}{\rho h}} \propto \frac{h}{R^2}$$

where $D = \frac{Eh^3}{12(1-v^2)}$ is the flexural rigidity.

Due to non-linearities, the resonance frequency shifts as a function of the applied voltages, which beneficially can be used to tune the transducer (a factor 4 is demonstrated).

The frequency of the cMUT is controlled by the following parameters:
 a) design parameters: R=membrane radius 332, as shown in FIG. 3
 b) material parameters: h=thickness; E=Young's modulus; V=Poisson ratio On a wafer, the thickness of dielectric layers and material constants are fixed.

The radius 332 of the cMUT 200 is used to control the frequency 310. Thus, it is possible to vary the frequency 310 within a single die and manufacture a broadband cMUT 200 that covers the entire frequency range targeted.

FIG. 3 further shows a graph of simulated response of air pressure 330 in capnography to capacitance 340 of the plates 220, 230 of a cMUT 200 capnography sensor. Greater air pressure 330 (here shown in units of bars) presses the plates 220, 230 closer, thereby increasing capacitance 340 (here shown in units of pF (picofarads)).

Another capacitive device that can be used for ultrasound send and receive is a MEMS microphone. This device is typically used for audio (for which you want a flat response), and it was intended for audio frequencies below 15 kHz. The assignee of the present patent application has found that the MEMS microphone can be operated in "resonant mode" at low Q-factor, of about unity, to thereby achieve a large bandwidth around, for example, 100 kHz, and that yet higher frequencies can be achieved by changing membrane parameters (such as its diameter, thickness and stress) to allow the gas measurement.

Figure 4:
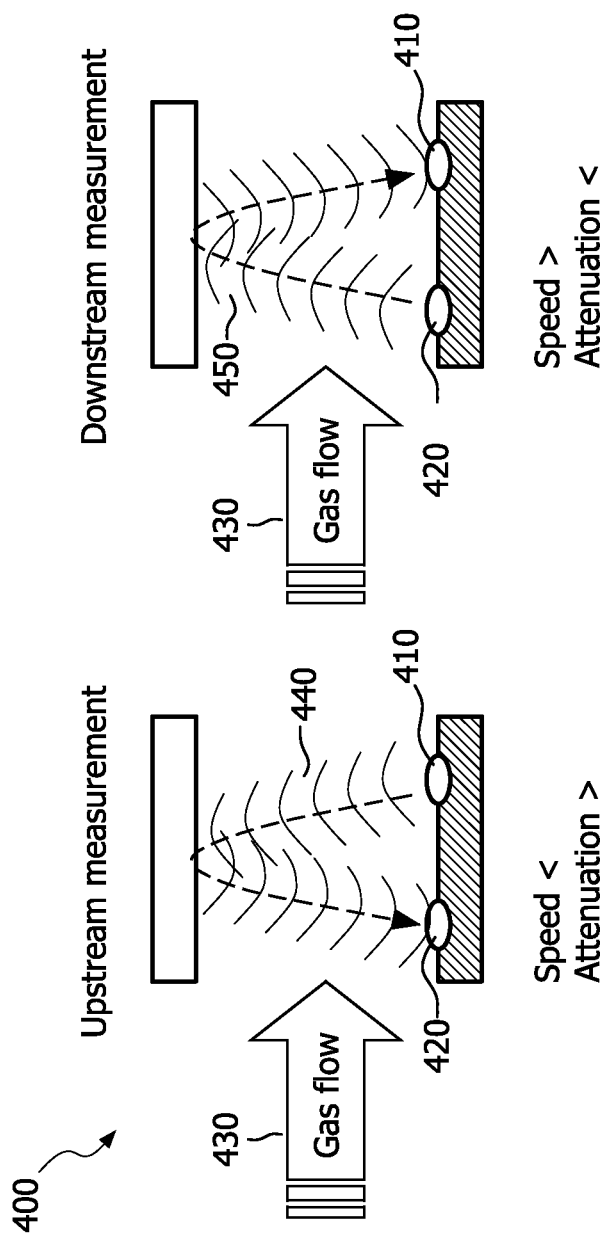
FIG. 4 is an exemplary conceptual diagram of flow measurement by upstream-downstream asymmetry, in accordance with the present invention.

FIG. 4 is an exemplary portrayal of flow measurement by upstream-downstream asymmetry, in accordance with the present invention. The flow 130 could be occurring in an airway or respiratory pathway which includes the tubing, mask or other paraphernalia leading to and coming from a respirator on which a medical subject is attached.

By combining a plurality of ultrasound transducers 200 on a single die (chip, flexible foil) the novel multi-gas analyzer system can determine the concentration 150 of a gas matrix in a broad range of temperature, pressure and flow regimes. All the macroscopic parameters, or a large subset of those parameters, are measured using one single chip comprising ultrasound devices only.

The air flow measurement is based on the fact that the ultrasound speed and/or absorption are different for upstream and downstream measurement. This effect, already known in gas-flow meters, is caused by an asymmetric effective ultrasound length changes in both directions of the flow 430. The method requires two or more ultrasound transducers 410, 420 placed in the flow 430. One transducer 410 emits a pulse 440 that is detected by the second transducer 420. Meanwhile or consecutively, a second pulse 450 is emitted from the second transducer 420 and detected by the first 410. Time-of-flight or signal amplitudes can then be compared.

Figure 5:
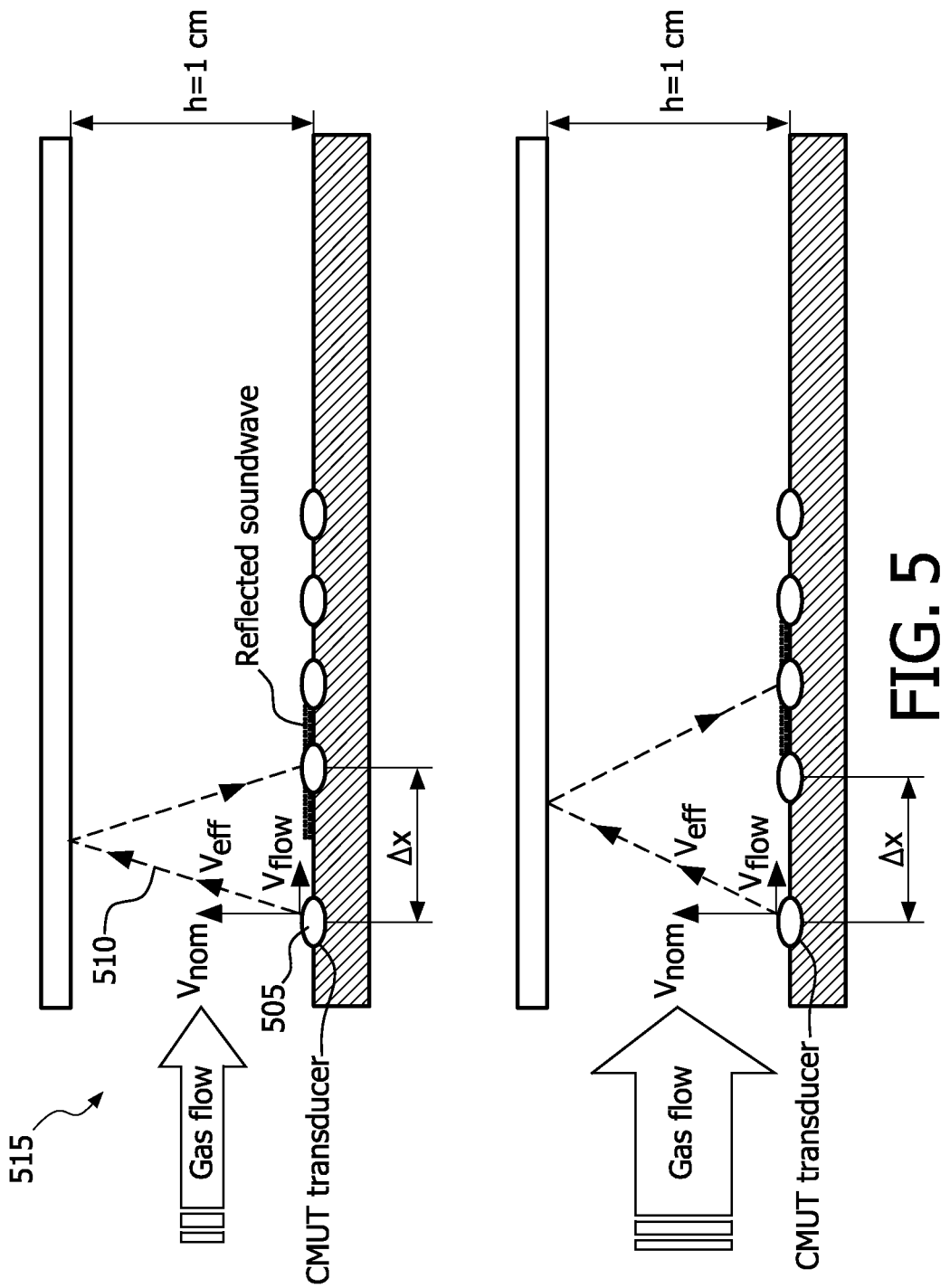
FIG. 5 is a conceptual diagram illustrating an example of flow measurement by sound wave displacement, in accordance with the present invention.

FIG. 5 illustrates an example of flow measurement by sound wave displacement, in accordance with the present invention. Flow is measured by determining displacement of the sound wave due to the horizontal air velocity caused by the flow.

A cMUT transducer 505 generates a diverging sound wave 510. At 100 ml/s (milliliters per second) gas flow in a 1×1 cm flow-chamber 515, the central point of the reflected sound wave is displaced over a distance $$\Delta x = 2h\frac{v_{flow}}{v_{nom}} = 60 \; \mu\text{m(microns)}.$$

By comparing the amplitude response using an array 205 of multiple transducers (typical diameter size 150~700 μm) at different positions, the displacement can be measured and used to calculate the flow. Note that the flow does not affect the time of flight of the central point of the sound wave, as the path length and the effective sound velocity scale both according to $$v_{eff} = \sqrt{v_{nom}^2 + v_{flow}^2}.$$

At each of the transducers both the time-of-flight and the amplitude is changed in response to flow variations.

Figure 6:
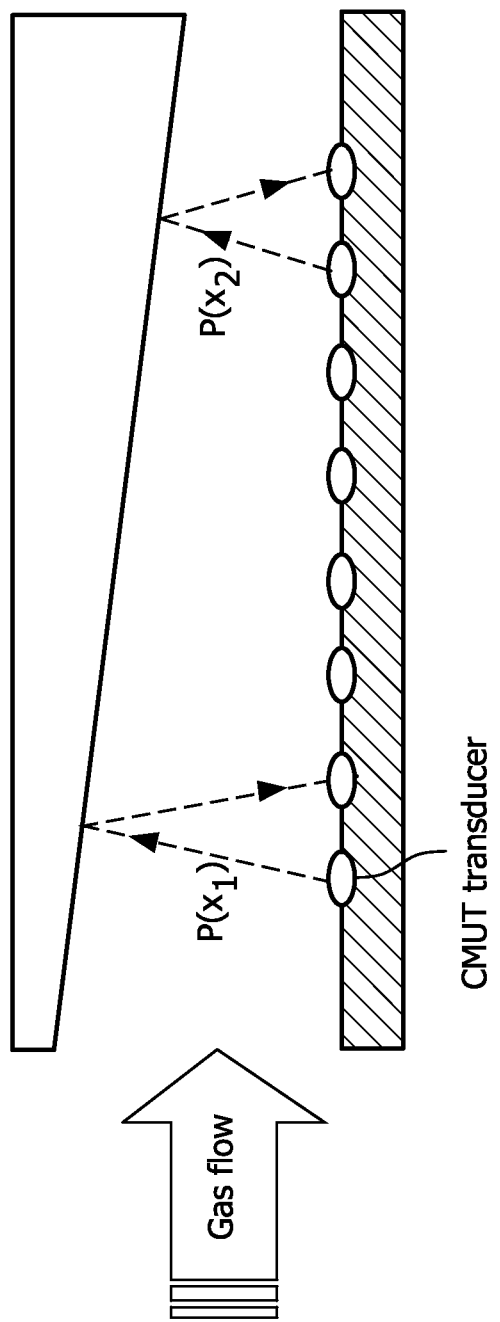
FIG. 6 is a conceptual diagram illustrating a particular version of restriction in air chamber cross-section to vary air pressure, in accordance with the present invention.

FIG. 6 shows a particular version of restriction in air chamber cross-section to vary air pressure, in accordance with the present invention.

This embodiment is based on the recognition that the ultrasound absorption spectrum changes with pressure 330. CMUT devices 200 are optimized for one single frequency 310 in order to retain their maximum efficiency. Tuning is effective over a +/−10% range, hence measuring over two decades require multi-cMUTs, which is a serious drawback in terms of the (1) limited number of discrete frequencies 310 (which may not be harmonic related), the (2) different footprint on the chip and (3) different driver hardware, etc.

In order to use the same cMUT devices 200 and measure at different frequencies 310, the pressure 330 is varied along the gas tube 515 by its cross section A (diameter, height).

The gas pressure 330 is governed by the equation:

$$p \propto v_{gas} \cdot A$$

where $v_{gas}$ is the gas velocity.

Extra pumping measures (vacuum) may be added to compensate for the flow resistance in the restriction.

Figure 7:
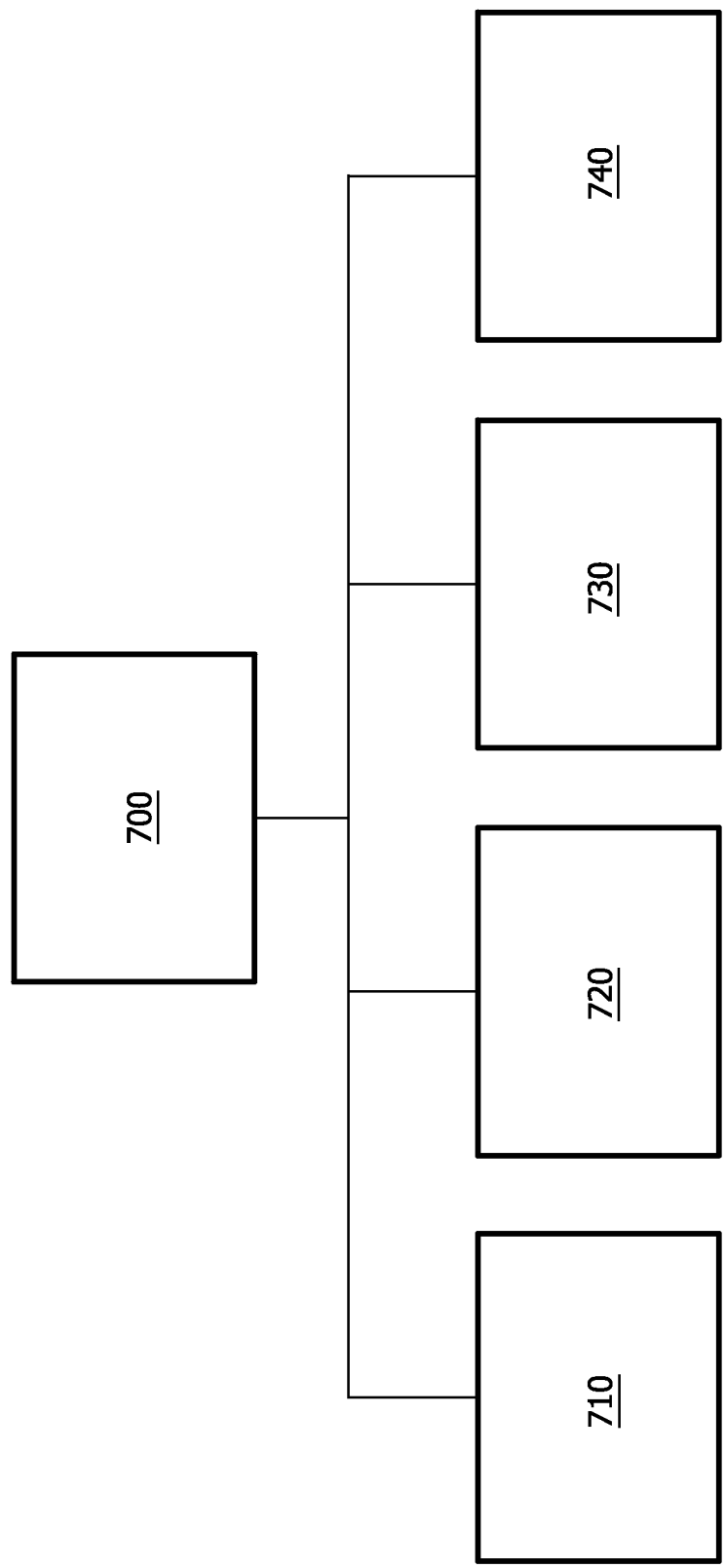
FIG. 7 is an exemplary conceptual diagram of an on-chip-implemented smart algorithm for parameter measuring on-chip, in accordance with the present invention.

FIG. 7 is an exemplary conceptual diagram of an on-chip-implemented smart algorithm for parameter measuring on-chip, in accordance with the present invention.

A smart algorithm 700 on-chip monitors on-chip elements whose existences depend on the implementation. Ones of cMUT transducers 200 may selectively be formed with either a vacuum-sealed cavity 710 or a gas-filled cavity 720. The chip may also include thermopiles (or resistive temperature-measurement elements) 730 and/or a radar element 740.

In the vacuum-sealed cavity 710 embodiment or portion of the embodiment, pressure 330 can be measured by a capacitive measurement of the average position of the plates 220, 230 in a cMUT transducer 200. As in standard air-pressure sensors, the plates 220, 230 of the cMUT transducer 200 are separated by a vacuum 235. The upper plate 230 is bent through the pressure difference between the vacuum 235 and the outer pressure 330, affecting the capacitance 340 of the plates 220, 230. The measurement of this capacitance 340 will consequently be indicative of the outer pressure 330.

By measuring the pressure difference at two locations, this method can also be used to measure the flow 130.

Temperature is a parameter that warrants measurement, because it affects global sound speed.

For the gas-filled cavity 720 embodiment or portion of the embodiment, temperature can be measured by a capacitive measurement of the average position of the plates 220, 230 in a cMUT transducer 200 where volume between the plates is filled by a gas. The upper plate is bent upwards when the temperature rises and the gas tries to expand, affecting the capacitance 340 of the plates 220, 230. The measurement of this capacitance 340 will consequently be indicative of the temperature.

As an alternative, on-chip thermopiles (or resistive elements) 730 may give a proper indication of the gas temperature.

The remainder of the parameters determinable by the smart algorithm 700 can be measured via the absorption and time-of-flight of the ultrasound, and their frequency dependence. Separate transducers as well as single transducers, like radar 740, may be used for transmitting and receiving signals. The quantity of water can be retrieved from the frequency shift of the $CO_2$ absorption maximum. The $N_2$ to $O_2$ ratio is retrieved in the absorption at higher frequencies.

Figure 8:
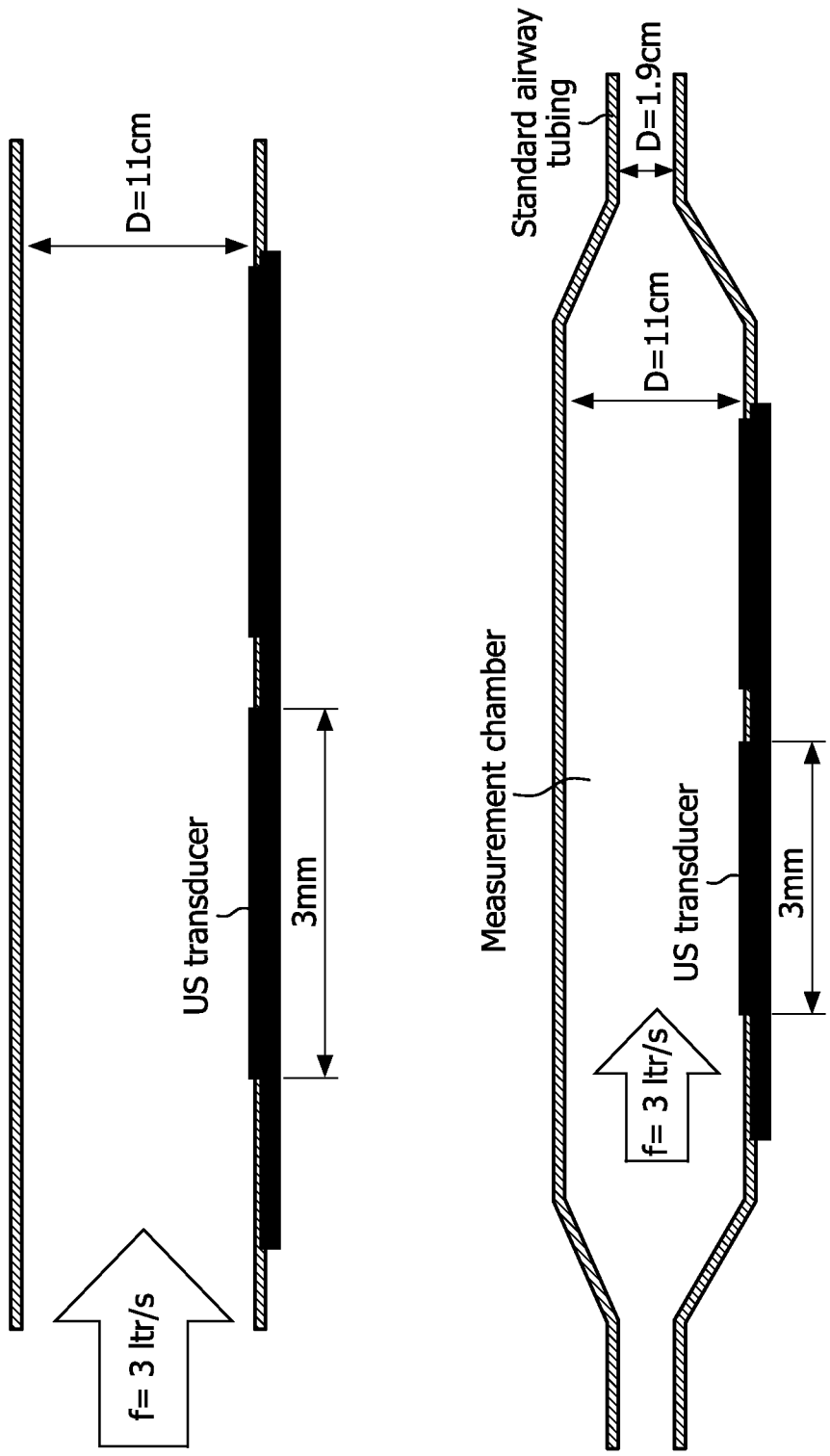
FIG. 8 is a schematic diagram portraying particular conceptions of a large diameter ultrasound chamber, in accordance with the present invention.

FIG. 8 features particular conceptions of a large-diameter ultrasound chamber 515, in accordance with the present invention.

In capnography, for example, to be compatible with small sized on-chip ultrasound transducers, what can be implemented is a virtual small ultrasound measurement chamber 515, which is fed with a small portion of the main airway flow 130 in order to realize a turbulence-free ultrasound measurement.

The term "airway system" must be interpreted broadly, in the context of either mainstream or sidestream applications. It comprises tubes, masks and other means to guide the breathing air of a living being. The term "respiratory pathway," as used herein, is likewise defined as comprising tubes, masks and other means to guide respiration.

The use of a tube design with low Reynolds numbers, at least in the measurement volume, ensures a stable flow and hence a stable signal inside the tube. A useful feature in a tube is rounded openings such as described in J. A. M. van de Nieuwendijk and J. E. M. Vael, "Bass-Reflex Port Measurements," Nat. Lab. Technical Note TN 065/97 and in "Alles wat ademt—R. de Nijs," EMI 1984.

Note that, since the occurrence of turbulence is a strongly nonlinear process, the same geometric feature in a tube will give rise to different degrees of turbulence depending on direction of flow in that tube. Flow in capnography can occur in two directions (inhaled and exhaled breath), and hence measures should be taken in such a way that they are appropriate for both directions of flow.

Features are constrictions, bends, corrugations, splits, etc. Impedance matching may be done by stubs or the like, but these are frequency/flow dependent. Non-resonant measures such as smoothly varying surfaces are another option.

Any measures reducing initial turbulence due to the respiratory phenomena of the subject, (i.e., human patient or animal), such as snoring are contemplated. For example a damper or active feedback can be used.

Further a turbulence indicator (for example based on sound propagation) could be used to fine tune the detailed gas flow 130 over the cross section of the tube in some controlled way by a device such as a valve.

When measuring in the full mainstream flow 130, the minimal diameter of the tubing must be increased, as shown in the top part of FIG. 8, from 1.9 cm to at least 10.5 cm in order to maintain laminar flow. As a result the dimensions of an ultrasound transducer 200 must scale appropriately to the 3 mm regime. The minimal tubing diameter constraint must be obeyed in at least the ultra-sound chamber 515.

In the next variation, shown underneath in FIG. 8, the 11 cm measurement chamber is gradually adapted to the 1.9 cm standard airway tubing.

Figure 9:
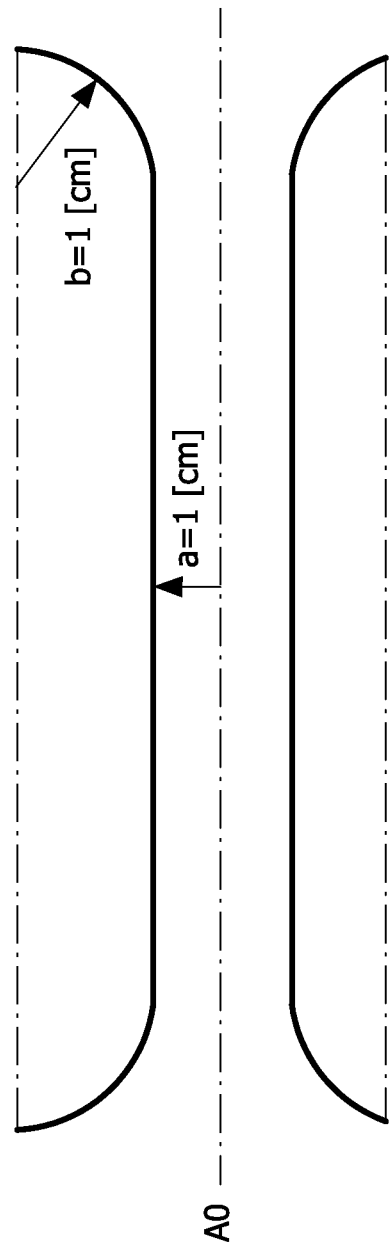
FIG. 9 is a schematic diagram of an optimal port contour, in accordance with the present invention.

FIG. 9 depicts a realization of an optimal port contour, in accordance with the present invention.

In the aforementioned Nieuwendijk et al. study it is concluded that the optimal port contour is a contour which slowly diverges towards both port ends with a maximum angle of 6 degrees (measured from port contour to port axis) and which is rounded with relatively small fillet radii at both port ends. This port geometry reduces the production of secondary noises (blowing noises, turbulence) by 8 dB. The port is rounded at both ends and slowly diverges at both ends.

FIG. 9 is taken from the Nieuwendijk et al. reference to illustrate a basic shape. In the present context, the scale should be taken smaller (for example: diameter 1 cm, total length 3 cm, radius 0.5 cm).

Figure 10:
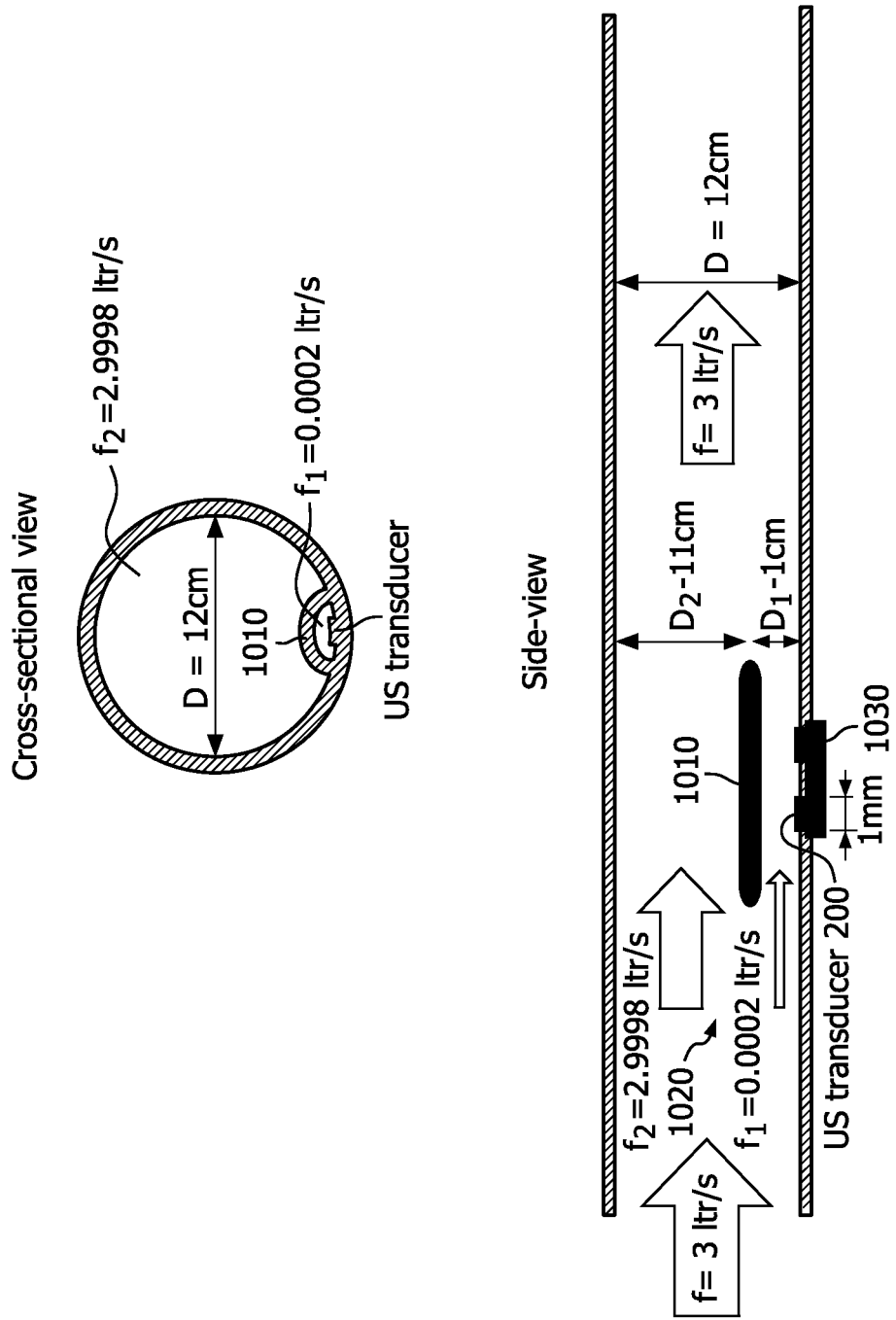
FIG. 10 is a structural and functional diagram of an underpass in the measurement chamber, showing a cross-sectional and a side view.

FIG. 10 depicts an underpass 1010 in the measurement chamber 515, showing a cross-sectional and a side view.

In order to further reduce the transducer size into the mm regime, a small fraction of the main flow is fed into a small sized ultrasound chamber by passive splitting 1020. The idea is shown in FIG. 10.

A small "underpass" 1010 at approximately 1 cm distance above the ultrasound chip 1030 in the wall of the 12 cm diameter pipe splits off a fraction $f_1$ of the main flow. In a rough estimation (neglecting the parabolic flow profile), the ratio between the flows is given by the formulas:

$$\frac{f_2}{f_1} = \left(\frac{D_5}{D_1}\right)^4, \text{ hence } f_1 = f\frac{(D_1)^4}{(D_1)^4 + (D_2)^4}$$

$$\text{and } f_2 = f\frac{(D_2)^4}{(D_1)^4 + (D_2)^4}$$

In practice a fraction of the main flow is "bent" across the ultrasound chip 1030. Due to the low flow across the chip 1030 substantial delay will low pass filter the sensor response. To overcome this problem two groups of transducers 200 used to (depending on the direction of the flow) measure where the air first enters the underpass 1010. The groups can be located on the same chip 1030.

Figure 11:
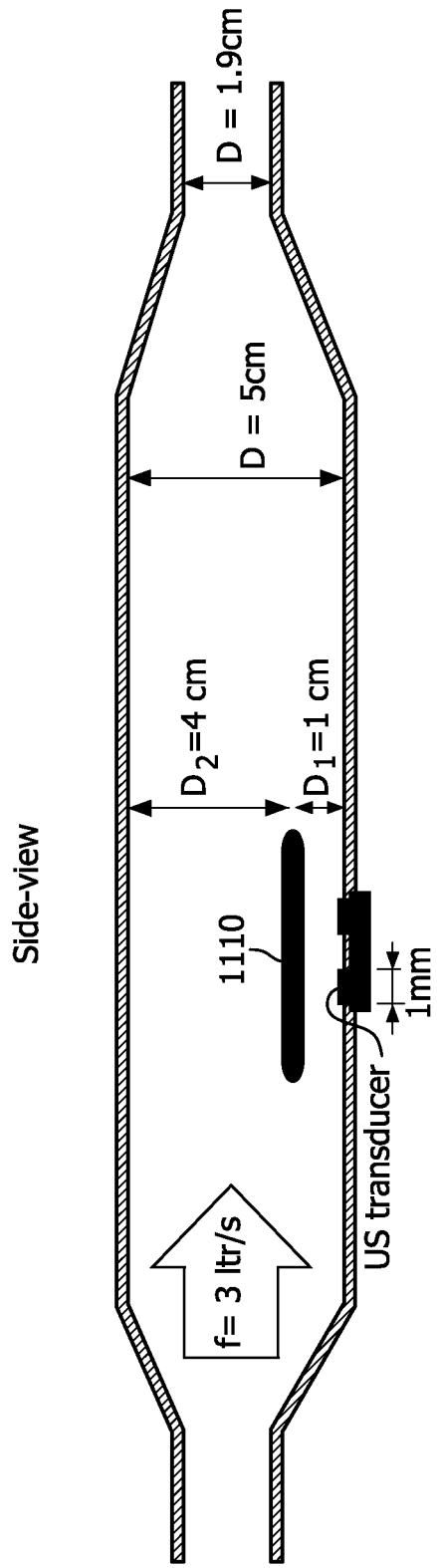
FIG. 11 is another version of the side view of FIG. 10 showing the tube with end tapering and decreased diameter throughout.

FIG. 11 is another version of the side view of FIG. 10 showing the tube 515 with end tapering and decreased diameter throughout.

The tube diameter may be gradually adapted from the standard ¾" tubing to 11 cm in the measurement chamber in order to realize pure laminar flow as mentioned above in connection with the FIG. 8 embodiment.

The function of the roof 1110 is three-fold: (a) reflector for the ultrasound signal; (b) splitter for the flow 130; and (c) damping of high-frequency turbulences, so that the main flow does not need to be perfectly laminar. As a result the measurement tubing diameter may be decreased to, for example, approximately 5 cm.

Figure 12:
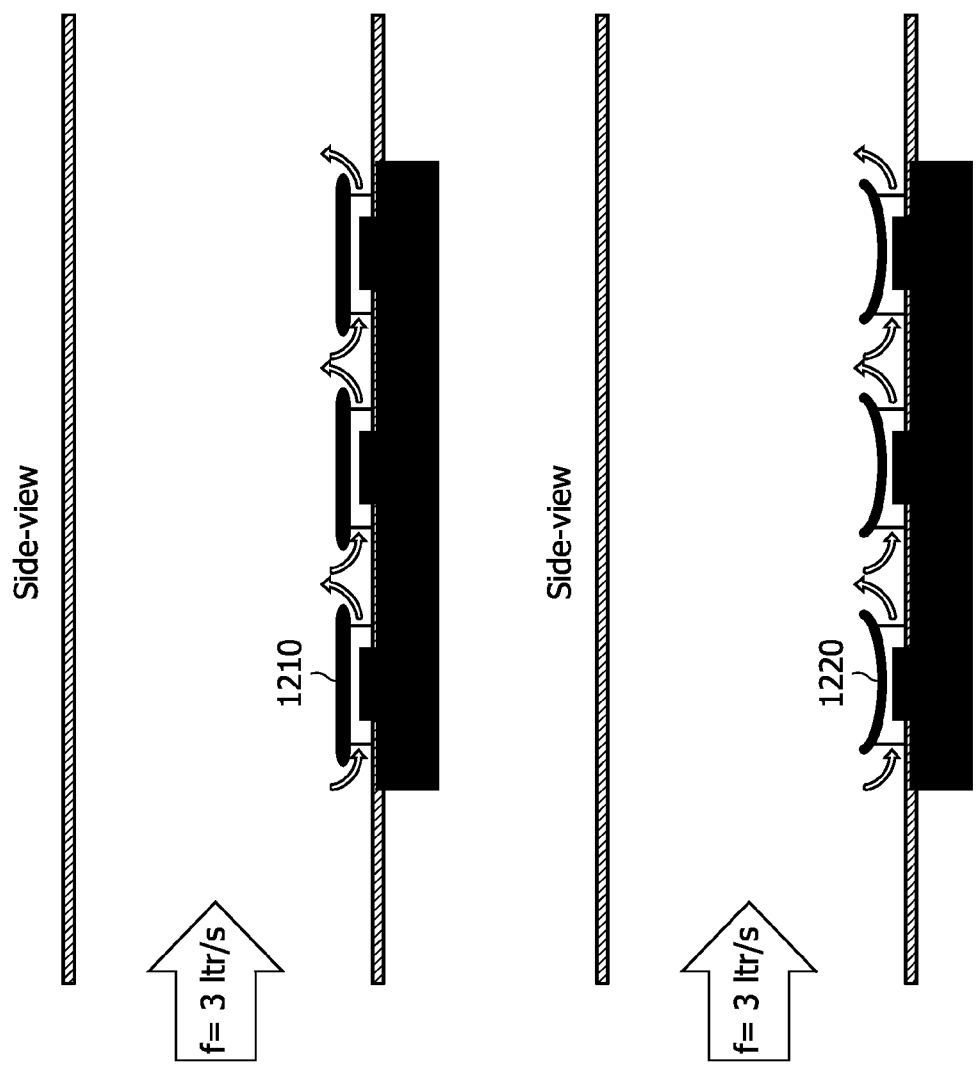
FIG. 12 is a conceptual diagram illustrating side views of on-chip roofs configured straight and for multi-reflections.

FIG. 12 illustrates side views of on-chip roofs 1210, 1220 configured straight and for multi-reflections.

In a further development the chip size can be reduced even further by implementing on-chip "roofs" 1210 in MEMS (micro electro mechanical systems) technology or other 1D/2D structure approximately 100 um above one or more transducers 200.

The roofs can have a streamlined contour in order to prevent turbulences.

Due to the small path length, the observed $CO_2$ signal may be small, which can be overcome by implementing multi reflections, e.g. via the adjacent roofs 1220, as shown in the bottom side-view of FIG. 12. This is easier when the transducers 200 become smaller ($D/\lambda \cong 1$) because of the more diverging wave front they generate.

Figure 13:
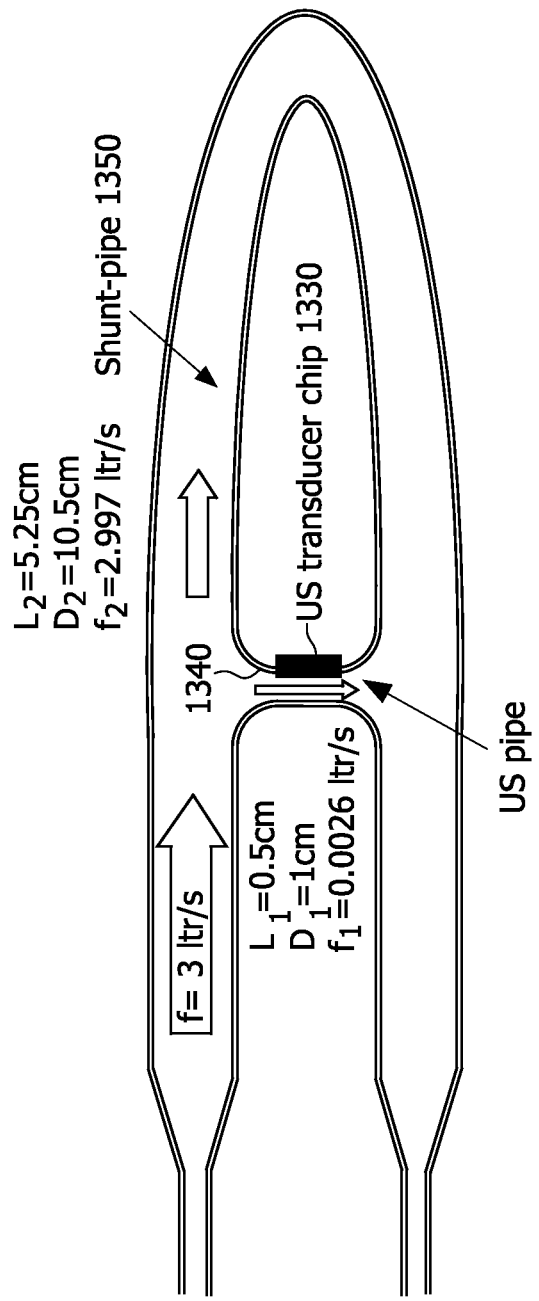
FIG. 13 is a schematic diagram exhibiting and example of a side view of shunt tubing for reducing turbulence in the vicinity of the sensor chip.

FIG. 13 exhibits an example of shunt tubing for reducing turbulence in the vicinity of the sensor chip 1330.

In a further embodiment, a small portion of the main flow 130 is split of by "short-cutting" a part of the main tube by a short, narrow tube 1340 where the ultrasound sensor chip 1330 is disposed.

The ratio between the flows is influenced by resistances of the two tubes 1340, 1350, which is given by the formulas:

$$\frac{f_2}{f_1} = \frac{L_1}{L_2}\left(\frac{D_2}{D_1}\right)^4, \text{ hence } f_1 = f\frac{L_1(D_2)^4}{L_2(D_1)^4 + L_1(D_2)^4}$$

$$\text{and } f_2 = f\frac{L_2(D_1)^4}{L_2(D_1)^4 + L_1(D_2)^4}.$$

The design is such that the delay (travel time of the air) in both pipes 1340, 1350 is equal (152 ms at 3 ltr/s) in order to avoid unequal arrival times which causes low-pass filtering of the response.

Sharp bending is avoided to reduce the risk of turbulences especially at the input and output of the ultrasound pipe.

To get rid of the delay due to the low flow in the ultrasound pipe 1340 and due to the dead volume in the shunt pipe 1350 (which low-pass filters the sensor response), transducers 200 are located at both sides of the chip 1330 as described in FIG. 10 embodiment.

Figure 14:
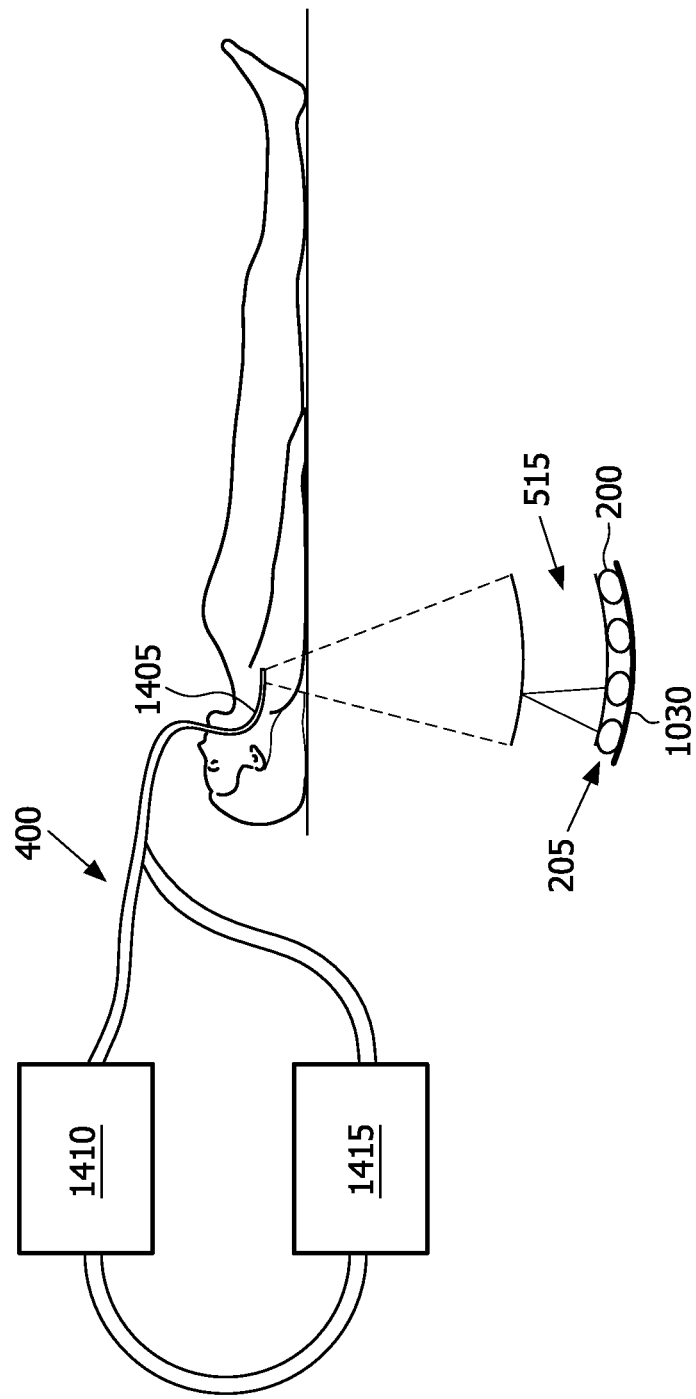
FIG. 14 is a conceptual diagram showing a measurement air chamber placed within a respiratory pathway, in accordance with the present invention.

FIG. 14 is a conceptual diagram showing a measurement air chamber 515 placed within a respiratory pathway 400, in accordance with the present invention.

In FIG. 14, exhaled breath 120 of a patient enters the tip of an ET (endotracheal) tube 1405. The expired breath 120 travels along the respiratory pathway 400 (which includes portions within the patient and portions outside the patient). First encountered is a $CO_2$ absorber 1410 for absorbing $CO_2$ from the incoming air stream. $O_2$ is pumped into the airstream by a ventilator 1415, which is attached to lead back along the respiratory pathway 400 to the patient. A similar cycle occurs within the patient. Blood in the lungs absorbs the newly supplied $O_2$ and releases $CO_2$ back into the respiratory pathway 400. The $CO_2$ laden air then travels up the ET tube 1405 and back to the $CO_2$ absorber 1410.

An expanded view of a portion of the ET tube 1405 shows a line of cMUTs 200, part of a cMUT array 205 on a sensor chip 1030. An ultrasound wave and its echo are shown, as in FIG. 5 for example.

This ventilator system may supply automatically, in addition to oxygen, the small supplements of anesthetic a patient receives during surgery.

Although capnography for a patient on a ventilator has been the focus herein, the novel multi-gas analyzer chip has other applications in medical care. For example, for a hospitalized patient breathing without assistance, the patient monitoring system may include the proposed gas sensor. Another application is within a portable, cardiopulmonary resuscitation (CPR) system.

Moreover, implementation in fields other than medical care is contemplated, such as those in which gas constituents are to be identified and quantified: in-building and automotive air quality, exhaust gas analysis, and advanced air control including environmental and greenhouse control.

It should be noted that the above-mentioned embodiments illustrate rather than limit the invention, and that those skilled in the art will be able to design many alternative embodiments without departing from the scope of the appended claims. For example, although cMUTs and MEMS microphone transducers have been discussed, the sensor chip may also feature piezo-based micromachined ultrasound transducers (PMUTs). In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed integrated circuit having a computer readable medium. The mere fact that certain measures are recited in mutually different dependent claims does not indicate that a combination of these measures cannot be used to advantage.

What is claimed is:

1. A sensor chip disposed within a measurement air chamber for analyzing a gas that comprises a plurality of components, said sensor chip comprising a plurality of cells for emitting and receiving ultrasound, wherein said sensor chip is configured for a frequency range and for measuring concentration of at least one of the plural gas components based on at least two ultrasound responses within said frequency range, wherein said measurement air chamber comprises a dimensional restriction in air chamber cross-section to vary a gas pressure in the measurement air chamber, wherein the dimensional restriction selectively varies cell-by-cell the gas pressure relative to a cell, to vary respective frequencies of the plurality of cells, to achieve said measuring of said concentration.

2. The sensor chip of claim 1, wherein the configuring for a frequency range comprises varying among the plural cells the respective frequencies.

3. The sensor chip of claim 2, wherein the plural cells have membranes for said emitting and receiving, each membrane having a size, wherein the membrane sizes and/or respective spring constants of said membranes differ among the plural cells so as realize said varying the respective frequencies.

4. The sensor chip of claim 2, wherein the plural cells have bias voltages, wherein said bias voltages differ among the plural cells so as to realize said varying of respective frequencies.

5. The sensor chip of claim 2, wherein, for said gas whose concentration is to be measured, a cell of said plurality of cells is sequentially tuned over a sufficiently broad range, by varying a bias voltage for said cell, to thereby retrieve different ones of said at least two ultrasound responses.

6. The sensor chip of claim 1, wherein said frequency range extends from 50 kHz to 10 MHz.

7. The sensor chip of claim 1, wherein a cell of said plurality of cells comprises a capacitive device.

8. The sensor chip of claim 7, wherein said capacitive device comprises a cMUT (capacitive micro machined ultrasound transducer).

9. The sensor chip of claim 7, wherein said capacitive device comprises a MEMS (micro electro mechanical systems) microphone.

10. The sensor chip of claim 1, wherein said sensor chip is configured for said measuring concentration of all of the plural components.

11. The sensor chip of claim 1, wherein said sensor chip is configured as a capnography sensor for measuring a level of carbon dioxide in exhaled breath.

12. The sensor chip of claim 1, wherein said sensor chip is designed for emitting ultrasound into air flowing across membranes of said cells, wherein said cells are arranged in a direction of air flow.

13. The sensor chip of claim 12, wherein said air flowing comprises exhaled breath, and wherein said sensor chip further configured for determining ultrasound time-of-flight for use in measuring of said concentration.

14. A measurement air chamber comprising a sensor chip for gas that comprises a plurality of components, wherein said sensor chip is configured with a plurality of cells for emitting and receiving ultrasound, wherein said sensor chip is configured for a frequency range and for measuring concentration of at least one of the plural gas components based on at least two ultrasound responses within said frequency range, wherein said sensor chip is configured to adjust to gas pressure in said chamber, and wherein said chamber is configured dimensionally to selectively vary cell-by-cell said gas pressure relative to a respective cell, to thereby vary frequencies of said cells, to achieve said measuring of said concentration.

15. A sensor chip disposed within a measurement air chamber for use in a respiratory pathway, said sensor chip comprising a plurality of ultrasound transducers for interrogating, by emitting and receiving ultrasound, so as to receive at least two ultrasound responses between 0.05 and 10 MHz, an on-chip algorithm device for combining said ultrasound responses to measure concentration of at least one air component in said respiratory pathway, wherein said measurement air chamber comprises a dimensional restriction in air chamber cross-section to vary a gas pressure in the measurement air chamber, wherein the dimensional restriction selectively varies, ultrasound transducer-by-ultrasound transducer, the gas pressure relative to an ultrasound transducer, to vary respective frequencies of the plurality of ultrasound transducers, to achieve said measuring of said concentration.

16. The sensor chip of claim 15, wherein a first of the plural ultrasound transducers emits a pulse that is thereafter detected by a second of the plural ultrasound transducers, and said second transducer emits a pulse that is thereafter detected by said first transducer, further wherein an air flow is measured based on comparison of the detected pulses.

17. The sensor chip of claim 15, wherein at least one of the plural ultrasound transducers is arranged in a direction of air flow across the sensor chip to receive return data of a diverging ultrasound wave, further wherein said on-chip algorithm device compares results of said at least one of the ultrasound transducer with respect to at least one of time-of-flight or amplitude, to measure said air flow.

18. The sensor chip of claim 15, wherein at least one ultrasound transducer of said plurality comprises a capacitive device having a pair of plates separated by a gap, further wherein said on-chip algorithm device measures capacitance for said pair of plates to thereby determine air pressure.

19. A method for measuring concentration of at least one component of a gas comprising that comprises a plurality of components within a measurement air chamber, the method comprising:
   providing a plurality of ultrasound transducer cells having membranes for emitting and receiving ultrasound and using the plurality of ultrasound transducer cells for receiving at least two ultrasound responses within a frequency range;
   dimensionally restricting the measurement air chamber in air chamber cross-section to vary a gas pressure in the measurement air chamber, wherein dimensionally restricting selectively varies cell-by-cell the gas pressure relative to a cell, to vary respective frequencies of the plurality of ultrasound transducer cells, to enable achieving a measure of said concentration; and
   measuring concentration of at least one of the plural components based on said at least two ultrasound responses.

20. An air-constituent measurement chip disposed within a measurement air chamber, comprising:
   an array of capacitive transducers having flexible membranes for emitting and receiving ultrasound, each membrane having a size,
   an on-chip algorithm device for measuring air flow using a plurality of said transducers in an air flow direction, said on-chip algorithm device further for measuring temperature by at least one of a capacitive measurement on transducer plates, a resistive element or an on-chip thermopile, wherein bias voltages of said transducers and/or the membrane sizes differ among said transducers so as to achieve an ultrasound frequency range and for measuring concentrations of nitrogen, oxygen, water and carbon dioxide in air, wherein said measurement air chamber comprises a dimensional restriction in air chamber cross-section to vary a gas pressure in the measurement air chamber, wherein the dimensional restriction selectively varies, transducer-by-transducer, the gas pressure relative to a transducer, to vary respective frequencies of the plurality of transducers, to achieve said measuring of said concentrations.

* * * * *